(12) United States Patent
Schnidrig

(10) Patent No.: US 8,281,656 B2
(45) Date of Patent: Oct. 9, 2012

(54) CARTRIDGE WITH FILL LEVEL DETECTION

(75) Inventor: Jürg Schnidrig, Diegten (CH)

(73) Assignee: Sensile Pat AG, Hagendorf (CH)

( * ) Notice: Subject to any disclaimer, the term of this patent is extended or adjusted under 35 U.S.C. 154(b) by 542 days.

(21) Appl. No.: 12/575,656

(22) Filed: Oct. 8, 2009

(65) Prior Publication Data
US 2010/0102799 A1    Apr. 29, 2010

(30) Foreign Application Priority Data

Oct. 27, 2008  (EP) .................................... 08167614

(51) Int. Cl.
*G01F 23/26* (2006.01)
(52) U.S. Cl. ......... 73/304 C; 73/658; 324/660; 417/44.1
(58) Field of Classification Search ............. 73/291–334
See application file for complete search history.

(56) References Cited

U.S. PATENT DOCUMENTS

| | | | |
|---|---|---|---|
| 4,638,670 A * | 1/1987 | Moser | 73/658 |
| 5,135,485 A | 8/1992 | Cohen et al. | |
| 5,704,922 A * | 1/1998 | Brown | 604/207 |
| 5,708,367 A * | 1/1998 | Tousson | 324/660 |
| 6,352,523 B1 | 3/2002 | Brown et al. | |
| 6,542,350 B1 | 4/2003 | Rogers | |
| 6,564,630 B1 * | 5/2003 | Klemp | 73/304 C |
| 6,859,673 B2 | 2/2005 | Steffen | |
| 7,511,480 B2 | 3/2009 | Steffen | |
| 2008/0152507 A1 * | 6/2008 | Bohm | 417/44.1 |

FOREIGN PATENT DOCUMENTS

| | | |
|---|---|---|
| DE | 102004040441 | 6/2006 |
| WO | WO 2005/005929 | 1/2005 |
| WO | WO 2006/021295 | 3/2006 |
| WO | WO 2007/107558 | 9/2007 |

* cited by examiner

*Primary Examiner* — Hezron E Williams
*Assistant Examiner* — Hoang Nguyen
(74) *Attorney, Agent, or Firm* — Saliwanchik, Lloyd & Eisenschenk

(57) ABSTRACT

A cartridge (2) with a fill level detection system (10, 10', 10"), the cartridge comprising a substantially rigid containing wall (4) having a tubular wall portion (12) surrounding a chamber (18) for receiving liquid therein, a plunger or piston (8) mounted inside the chamber and configured to seal one side of the chamber, the plunger or piston being displaceable in the chamber towards an outlet end (14) of the cartridge, characterized in that the fill level detection system comprises a plurality of discrete fixed electrodes (24, 24') positioned along the tubular wall portion in a juxtaposed manner in a direction of displacement D of the plunger or piston (8), and a mobile electrode member (28) fixed to the plunger or piston and displaceable therewith.

14 Claims, 3 Drawing Sheets

CARTRIDGE WITH FILL LEVEL DETECTION

FIELD OF THE INVENTION

The present invention relates to a cartridge for containing fluids, with a fill level detection system. The invention in particular relates to a cartridge for liquid medicinal products, such as insulin, glucagon, and growth hormones, the cartridge comprising a mobile piston or plunger for expelling the liquid or simply allowing a change in volume in the cartridge.

BACKGROUND

Cartridges with a piston or plunger are well-known in insulin pump systems whereby detection of the fill level of the cartridge is important to ensure that the pump system functions correctly and/or that the correct dosage is supplied and/or to signal replacement of the cartridge.

Various cartridge fill level detection systems have been proposed as described in U.S. Pat. No. 5,704,922, U.S. Pat. No. 6,352,523, WO 2007/107558, and DE 102004040441.

In U.S. Pat. No. 5,704,922, a syringe having electrical contacts points for metering doses is disclosed. A disadvantage of this system is the risk of short-circuiting between contacts leading to a false fill level reading. Moreover, in view of the difficulty of providing a large number of contacts, the fill level accuracy of the system is poor. The need to connect the contacts on the plunger requires a connector that is costly and voluminous.

Some of these drawbacks are overcome by contactless fill level detection systems as described for example in U.S. Pat. No. 6,352,523, DE 102004040441 or WO 2007/107558. In these known systems, electrodes are positioned on either side of the cartridge to measure the capacitance which is dependent, inter alia, on the dielectric properties between the electrodes. The dielectric properties depend on the material forming the cartridge walls, the distance separating the electrodes, the material of the plunger, the dielectric value of the liquid in the cartridge and the fill level. As the liquid in the cartridge has a dielectric properties that are different to air and the material of the plunger, the overall capacitance value will vary as the plunger advances and liquid is expelled out of the cartridge. One of the major drawbacks of this measuring system is its sensitivity to interference, and the need to accurately calibrate the system in view of the reliance on many factors affecting the capacitance measurement. The accuracy and reliability of such a system may in many applications be insufficient. Also, the need to adjust calculation of the measurement and to calibrate the cartridge fill level detection as a function of the diameter of the cartridge and the material used for the cartridge as well as the properties of the liquid in the cartridge, is costly.

SUMMARY OF THE INVENTION

In view of the aforegoing, it is an object of this invention to provide a cartridge for fluid storage and delivery, with an accurate and reliable fill level detection system.

It would be advantageous to provide a cartridge with fill level detection that is economical.

It would be advantageous to provide a cartridge with fill level detection that may be implemented in cartridges of different sizes, shapes and materials that is easy to configure and calibrate.

Objects of this invention have been achieved by providing the cartridge with fill level detection according to claim 1.

Disclosed herein is a cartridge comprising a substantially rigid containing wall having a tubular wall portion surrounding a chamber for receiving liquid therein, a mobile plunger or piston mounted inside the chamber and configured to seal one side of the chamber, the plunger or piston being displaceable from a plunger end of the tubular wall portion to an outlet end of the tubular wall portion for allowing the liquid to be expelled out of the chamber, and a capacitive fill level detection system, characterised in that the fill level detection system comprises a plurality of discrete fixed electrodes positioned along the tubular wall portion in a juxtaposed manner in the direction of displacement of the plunger or piston, and a complementary mobile electrode member fixed to the plunger or piston and displaceable therewith. The position of the plunger/piston, and thus the fill level of the fluid in the chamber, is determined by reading the capacitance value between each of the plurality of fixed electrodes positioned along the tubular wall portion, and the complementary mobile electrode on the plunger/piston, whereby the fixed electrode that provides the strongest signal indicates the position of the plunger electrode.

The signals from the plurality of fixed electrodes may by read simultaneously or sequentially. Preferably, the plurality of fixed electrodes on the tubular wall portion are connected to a multiplexer configured to activate and read the plurality of electrode sequentially from one end of the tubular wall portion to the other end or in any chosen order.

Advantageously, the fill level detection system according to the invention does not depend on the material properties, shape, and dimensions of the cartridge components and the liquid contained therein and is thus particularly reliable and robust. Also, fill level detection can be easily implemented in cartridges of different sizes, shapes and materials for use with different liquids, easily and with little or no calibration.

Further objects and advantageous aspects of the invention will be apparent from the claims and the following detailed description and annexed drawings.

BRIEF DESCRIPTION OF THE DRAWINGS

FIG. 1a is an illustration of a cartridge with fill level detection system according to an embodiment of this invention.

FIG. 1b is a simplified cross-sectional view through the cartridge of FIG. 1a.

FIG. 1c is a simplified graph illustrating the envelope of an electrical signal response of the fixed electrodes of the fill level detection system of FIG. 1a.

FIG. 2a is a simplified illustration of a cartridge with fill level detection system according to another embodiment of this invention.

FIG. 2b is a simplified cross-sectional view through the cartridge of FIG. 2a.

FIG. 2c is a simplified graph illustrating the envelope of a signal response for the fixed electrodes of the embodiment of FIG. 2a.

FIG. 3b is a simplified graph illustrating the envelope of a signal response for the fixed electrodes of the embodiment of FIG. 3a.

Figures 1A, 1B:
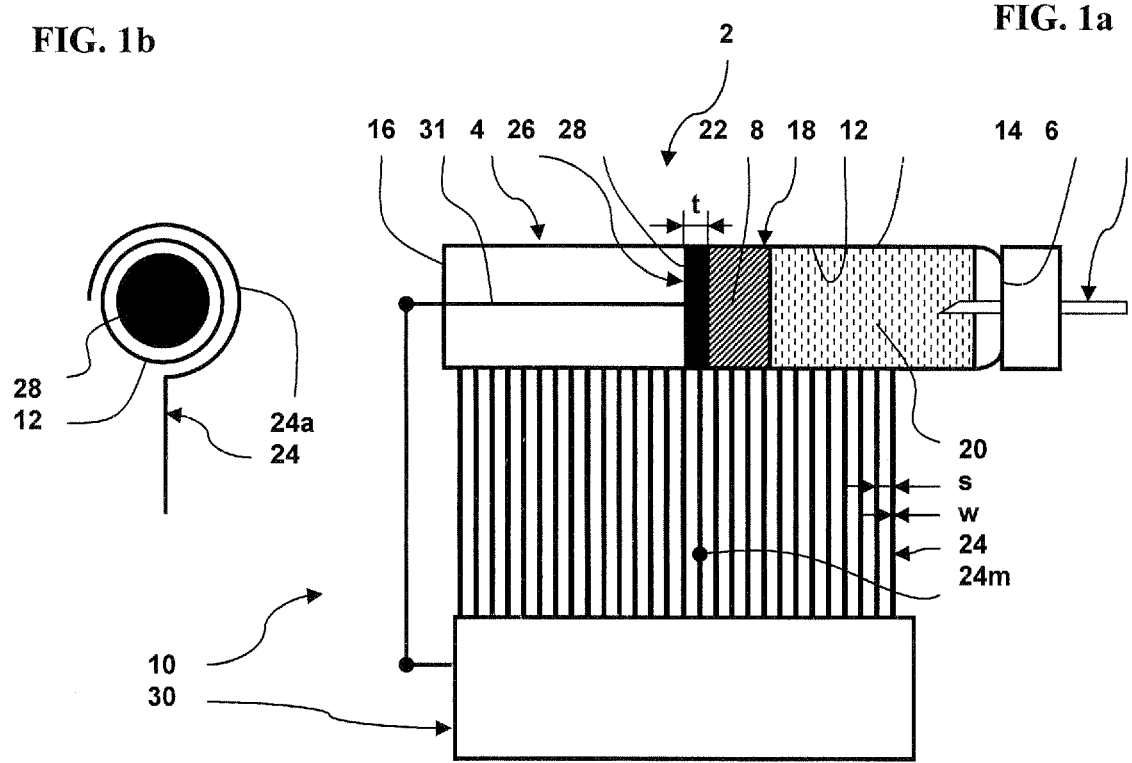

Referring to the Figures, a cartridge 2, 2', 2" comprises a container wall 4, an outlet 6, a plunger or piston 8, and a fill level detection system 10, 10', 10".

DETAILED DESCRIPTION OF EMBODIMENTS OF THE INVENTION

The container wall 4 comprises a tubular wall portion 12 extending from an outlet end 14 to an opposed plunger end 16 proximate a starting position of the plunger/piston 8 when the cartridge is full. The outlet end 14, tubular wall portion 12 and plunger/piston 8 define a chamber 18 storing a fluid 20 that is expelled though the outlet 6 when the plunger/piston is advanced towards the outlet end 14. The tubular wall portion 12 thus extends in a direction of displacement D of the plunger or piston and preferably has a cylindrical shape.

The cartridge 2, 2', 2" may for example be in the general form of a vial for the storage and delivery of a liquid medicine such as insulin, the cartridge being replaceably installed in a delivery system, for instance an insulin pump device. The cartridge may also be non-replaceable and refilled, for example through a valve or a seal, from a separate liquid source.

The outlet end 14 of the cartridge may for example be in a form of a cap with an aseptic self-sealing membrane that is pierced by a needle that forms the outlet 6 of the cartridge. The needle 6 may be connected to a system for delivery of a liquid medicine, such as insulin, to a patient.

The plunger/piston 8 may comprise a stopper with elastic sealing rings, or a stopper integrally made of an elastic material, for instance silicon rubber.

The cartridge tubular wall portion 12 may be made of glass, a plastic material or other non-conductive materials suitable for the fluid 20 that is contained in the cartridge.

The fill level detection system 10, 10', 10" comprises a plurality of discrete fixed electrodes 24, 24' arranged in a juxtaposed manner along the tubular wall portion 12 in the direction D of displacement of the plunger 8, and a complementary electrode 26 comprising a conductive mobile discrete electrode member 28 fixed to the plunger/piston 8.

The mobile discrete electrode member 28 is preferably in a form of a substantially planar disc that has a shape that essentially corresponds to the cross-sectional profile of the chamber 18. The mobile discrete electrode member may however be provided in other shapes and sizes without departing from the scope of the invention. The mobile discrete electrode member 28 may be attached, for example bonded, to a rear side of the plunger/piston opposite the liquid filled side of the chamber. The mobile discrete electrode member may however be mounted within the plunger/piston by overmoulding, assembling in a corresponding cavity in the plunger/piston, or mounted on the liquid contacting side of the plunger/piston 8. The mobile discrete electrode member 28 may be in the form of a metallic disk that is mounted to the plunger/piston, or could be in the form of a conductive layer deposited on a substrate or directly on a surface of the plunger/piston. The mobile discrete electrode member could also be in a form of a conductive material layer that is formed or deposited in an injection molding or casting process during which the plunger or piston is also formed.

The fill level detection system further comprises a signal processing circuit 30 connected to the plurality of fixed electrodes 24, 24' and the complementary mobile electrode member 28 and configured to send an electrical signal to the electrodes and to read the response thereof. The signal processing circuit, in a preferred embodiment, comprises a signal multiplexer and/or demultiplexer for sending and/or receiving electrical signals to each of the plurality of discrete fixed electrodes 24, 24'. The fixed electrodes 24, 24' can be used either as a receiver or as a sender of the electrical measurement signal whereby the complementary electrode 26, 26', 26" may act as a receiver if the discrete plurality of electrodes act as senders, or as a sender if the discrete plurality of electrodes act as receivers.

Figure 1C:
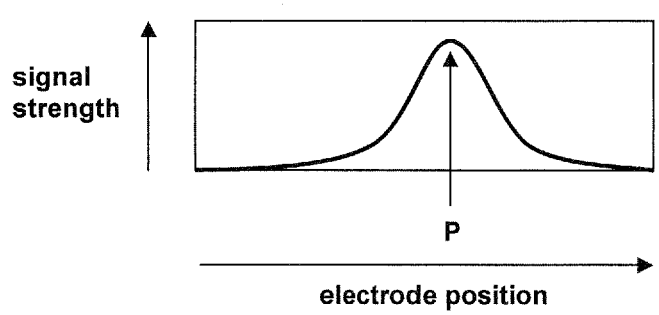

The multiplexer/demultiplexer 30 enables an electrical signal to be applied to the plurality of fixed electrodes 24, 24' sequentially, i.e. one after the other, and to determine the electrical signal response for each of the fixed electrodes 24, 24' whereby the peak signal P will occur for the discrete fixed electrode 24m, 24m' positioned closest to the mobile electrode member 28 as best illustrated in FIG. 1c in conjunction with 1a, 2c in conjunction with 2a, and 3b in conjunction with 3a. As the signal response strongly depends on the position of the mobile electrode member 28, and thus on the plunger/piston position, but not on the dimensions and dielectric properties of the cartridge the fluid, the position of the plunger/piston may be determined reliably and with a high tolerance to external noise, temperature or other factors that may affect reading of a capacitance value.

Referring in particular to FIGS. 1a, 1b, the plurality of discrete fixed electrodes 24 may advantageously comprise electrode portions 24a that wrap around the tubular wall portion 12 of the cartridge partially, for example as shown in FIG. 1b, or completely (not shown). In the case of a cylindrical tubular cartridge as illustrated, the electrode portions 24a would thus form partial or complete rings arranged coaxially around the chamber 28 through which the plunger/piston 8 is displaced.

The spacing s between adjacent fixed electrodes 24, 24' and the width w of each electrode in the direction of displacement D of the plunger/piston may be adjusted to take into account the number of electrodes per unit length of cartridge, the spacing required between adjacent electrodes for electrical insulation or decoupling of capacitive effect, or to take into account the signal strength. In other terms, the geometry of the fixed electrodes may be adjusted to optimize the peak signal P reading. The thickness t of the mobile discrete electrode member 28, in the plunger/piston displacement direction D, may be determined empirically for optimal signal accuracy, robustness and strength. Preferably, the thickness t of the mobile electrode member is less than double the spacing s between adjacent fixed electrodes 24, 24' more preferably less than 1.5 times the spacing s between adjacent fixed electrodes.

The fixed electrodes 24, 24' may be in the form of conductors embedded by overmolding or casting in the material forming the tubular wall portion of the cartridge during formation thereof. The wrap around portions 24a, 24a' of the fixed electrodes could also be deposited on a layer inside, or on an outer layer of the tubular wall portion 12, by various known metal deposition processes. Fixed electrodes could, in yet another variant, be formed on a separate substrate, for example a flexible substrate or a thermoformable substrate that is wrapped around and bonded or fixed by other means to the cartridge container wall 4, whereby the signal processing circuit may also be integrally formed on the substrate or alternatively connected thereto via a connector on the substrate or by other known interconnection means for flexible printed circuits.

The discrete fixed electrodes 24, 24' could also be formed on or within a housing with a cavity corresponding to the outer shape of the cartridge so that the housing (not shown) may by inserted over the cartridge as a single piece or assembled therearound by splitting the housing into two pieces or alternatively by having a single housing with essentially U-shape cavity that is mounted in a direction orthogonal to the displacement direction D over the cartridge tubular wall portion 12.

Therefore, the fixed electrodes may be formed in or on the tubular wall portion 12 of the cartridge or on a separate member that is positioned partially or completely around the tubular wall portion 12.

Figure 3A:
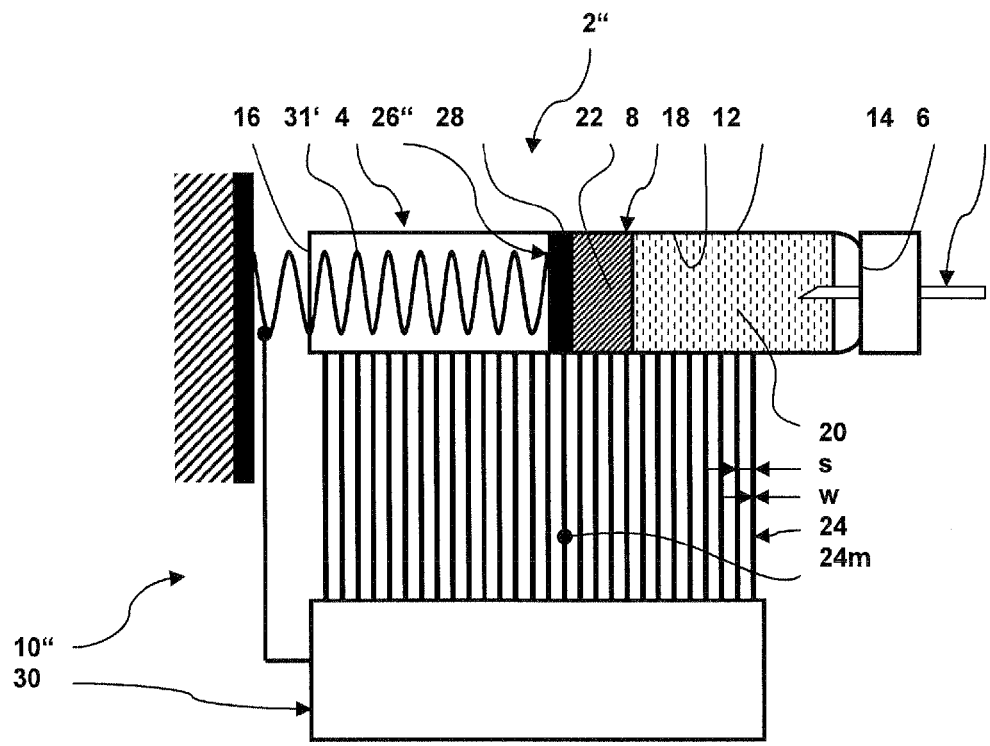
FIG. 3a is a simplified illustration of a cartridge with fill level detection system according to yet another embodiment of this invention.
Figure 3B:
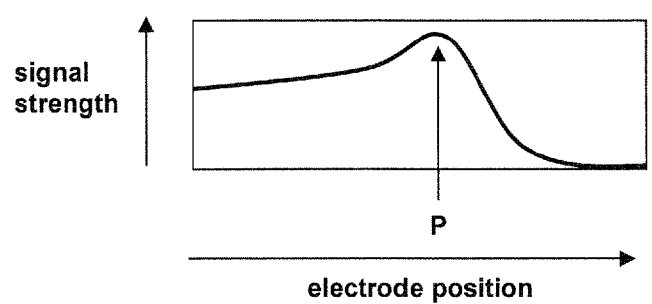

In the embodiment of FIGS. 1a to 1c, the mobile electrode member 28 is connected directly to the signal processing circuit 30 by means of a conductor lead 31 which may be an insulated wire conductor. In other variants, the mobile electrode member may be electrically connected to the signal processing circuit 30 via a plunger push rod made of or comprising a conducting material connected at its other end to the signal processing circuit, or via a piston plunger push spring 31' made of or comprising a conducting material as illustrated in the embodiment of FIGS. 3a, 3b.

Figures 2A, 2B:
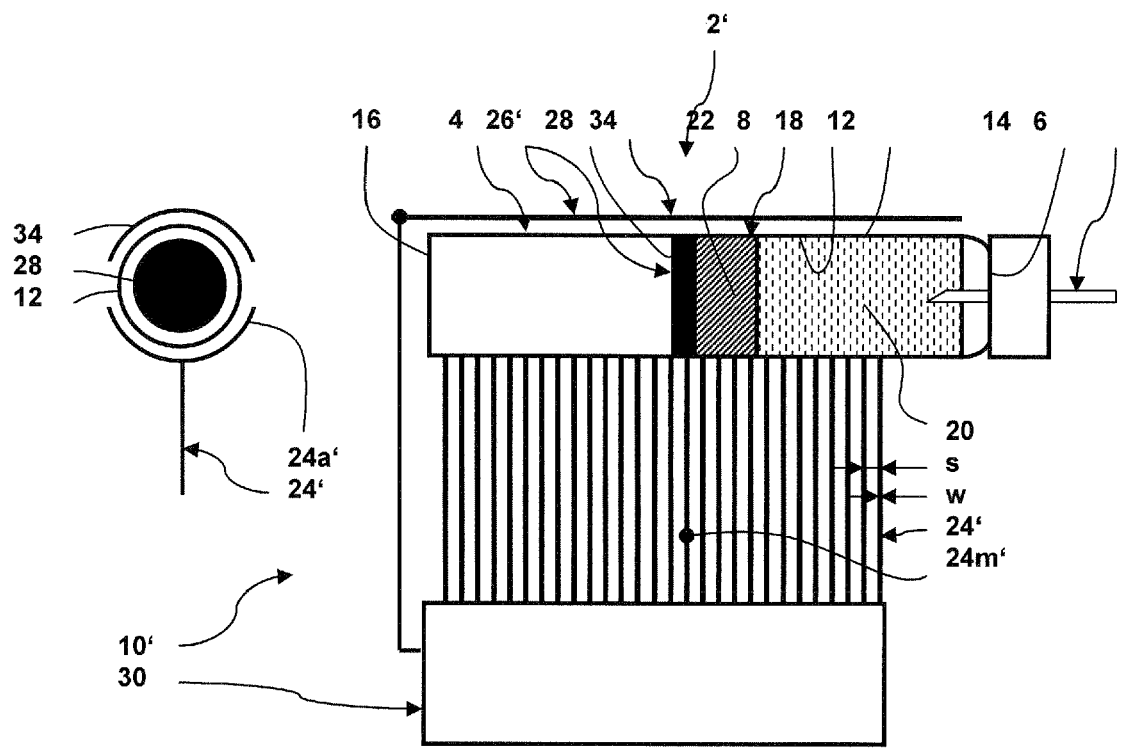
Figure 2C:
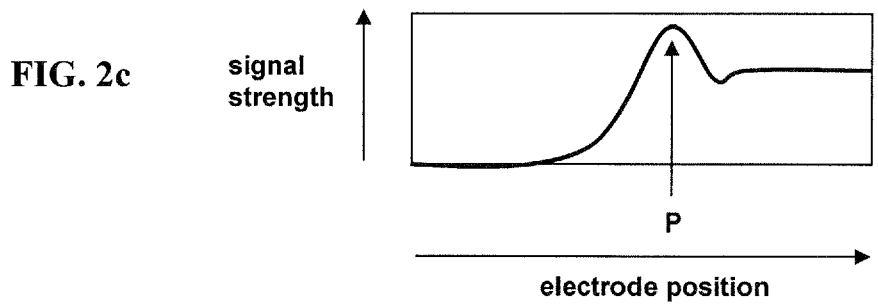

Referring to FIGS. 2a to 2c, the complementary mobile electrode member 28 is capacitively coupled to a conductor 34 of the complementary electrode 26' extending along the cartridge in the direction of displacement D and positioned on an opposite side of the cartridge containing wall 4 from the discrete fixed electrodes 24', the conductor 34 being interconnected to the signal processing circuit 30. An advantage of this embodiment is that the mobile electrode member 28 does not require a direct electrical interconnection, whereby the electrical interconnection of the complementary electrode conductor 34 and the discrete fixed electrodes 24' to the signal processing circuit may be performed without any interconnections to moving parts. The complementary electrode conductor 34 thus acts as a capacitively coupled electrode with respect to the mobile discrete electrode member 28.

It would also be possible, within the scope of this invention, to split the complementary electrode conductor 34 into a plurality of discrete fixed electrodes arranged opposite the fixed electrodes 24' in order to form juxtaposed pairs of opposing electrodes interconnected to the multiplexer circuit 30. In the latter variant, the mobile discrete electrode member 28 would act as a capacitive coupling element between respective pairs of opposed electrodes arranged either side of the cartridge cavity.

As illustrated in the embodiment of FIG. 2b, the fixed electrodes 24' and opposed complementary electrode conductor 34 (or opposed fixed electrodes with reference to the above described variant) may each wrap around less than half the perimeter of the tubular wall portion 12 of the cartridge.

The complementary electrode conductor 34 may be mounted or deposited on the cartridge by any of the various techniques mentioned above with respect to the fixed electrodes 24, 24'.

I claim:

1. A cartridge with a fill level detection system, the cartridge comprising a substantially rigid containing wall having a tubular wall portion surrounding a chamber for receiving fluid therein, a plunger or piston mounted inside the chamber and configured to seal one side of the chamber, the plunger or piston being displaceable in the chamber towards an outlet end of the cartridge, wherein the fill level detection system comprises a plurality of discrete fixed electrodes positioned along the tubular wall portion in a juxtaposed manner in a direction of displacement D of the plunger or piston, and a mobile discrete electrode member fixed to the plunger or piston and displaceable therewith, the average thickness (t) of the mobile discrete electrode member in the direction of displacement of the mobile electrode member being equal to, or less than, two times a spacing (s) between adjacent said discrete fixed electrodes.

2. The cartridge with fill level detection system according to claim 1, wherein the fill level detection system comprises a signal processing circuit connected to the plurality of discrete fixed electrodes, the signal processing circuit comprising a multiplexer for sequentially transmitting and/or receiving signals to each of the plurality of discrete fixed electrodes.

3. The cartridge according to claim 1 wherein the mobile discrete electrode member is directly electrically connected by means of a conductor to a signal processing circuit.

4. The cartridge according to claim 1 wherein the mobile discrete electrode member is connected to a signal processing circuit via a capacitive coupling to a complementary electrode conductor electrically connected to said signal processing circuit.

5. The cartridge according to claim 4 wherein the complementary electrode conductor extends along the tubular wall portion in the direction of displacement D of the mobile discrete electrode member on a side of the cartridge containing wall essentially opposite the plurality of discrete fixed electrodes.

6. The cartridge according to claim 1 wherein the mobile discrete electrode member comprises an electrically conductive disk shaped element assembled to the plunger or piston.

7. The cartridge according to claim 1 wherein the plurality of discrete fixed electrodes each comprise an electrode portion wrapped around the tubular wall portion more than 180°.

8. The cartridge according to claim 1 wherein the plurality of discrete fixed electrodes each comprise an electrode portion wrapped around the tubular wall portion less than 180°.

9. The cartridge according to claim 1 wherein the plurality of discrete fixed electrodes are formed on a substrate assembled to the cartridge containing wall.

10. The cartridge according to claim 9 wherein the substrate is a flexible thin film.

11. The cartridge according to claim 9 wherein the substrate is in the form of a housing injected or molded from an insulating material such as plastic.

12. The cartridge according to claim 1 wherein the plurality of discrete fixed electrodes have electrode portions (24a, 24a') formed directly on or in the cartridge containing wall (4).

13. A method of determining the fill level of a cartridge comprising a mobile plunger or piston, including:
providing the cartridge with a plurality of discrete fixed electrodes positioned along a tubular wall portion of the cartridge in a juxtaposed manner in a direction of displacement D of the plunger or piston, and a mobile discrete electrode fixed in, on or to the plunger or piston, and
reading a capacitance value between each of the plurality of fixed electrodes and the mobile discrete electrode, whereby the fixed electrode that provides the strongest capacitance value indicates the position of the plunger or piston,
wherein the average thickness (t) of the mobile discrete electrode member in the direction of displacement of the mobile electrode member being equal to, or less than, two times a spacing (s) between adjacent said discrete fixed electrodes.

14. The method according to claim 13 wherein the capacitance value between each of the plurality of fixed electrodes and the mobile electrode are read sequentially by means of a multiplexer.

* * * * *